United States Patent [19]

Lay, deceased et al.

[11] 4,167,188

[45] Sep. 11, 1979

[54] SURGICAL ELASTIC BAND

[76] Inventors: Coy L. Lay, deceased, late of Lakeland, Fla.; Madeline R. Lay, administratrix, P.O. Box 1429, Lakeland, Fla. 33802

[21] Appl. No.: 750,003

[22] Filed: Dec. 13, 1976

[51] Int. Cl.$^2$ ............................................ A61B 17/12
[52] U.S. Cl. .................................................... 128/326
[58] Field of Search .................. 128/303 A, 325, 326, 128/DIG. 21; 15/210 B; 308/238, 325, 326, 303 A, 327

[56] References Cited

U.S. PATENT DOCUMENTS

| | | | |
|---|---|---|---|
| 1,533,441 | 4/1925 | Melling | 128/327 UX |
| 2,619,964 | 12/1952 | Thaete | 128/326 X |
| 2,851,314 | 9/1958 | Thomson | 308/238 |
| 3,911,923 | 10/1975 | Yoon | 128/303 A |

Primary Examiner—Robert W. Michell
Assistant Examiner—Milford Juten
Attorney, Agent, or Firm—James J. Brown

[57] ABSTRACT

An improved elastic band is disclosed having dimensions and design specifically adapted for tying off human fallopian tubes or similar internal, tubular members. The band of the present invention has an internal diameter at least about 50% larger than the diameter of similar bands previously employed and ranges from 1.4 to 2.2 mm. The length or thickness of the band is at least 50% greater than the internal diameter of the band; and, in a preferred embodiment, the internal diameter of the band at both ends is about 0.2 to 0.6 mm. smaller than the internal diameter at the mid portion of the band. Thus, in a preferred embodiment, the internal diameter of the tube at its mid portion is 1.8-2.2 mm, at both ends is 1.4 to 1.8 mm, and the length of the band is 2 to 3.5 mm.

6 Claims, 4 Drawing Figures

SURGICAL ELASTIC BAND

The present invention is concerned with elastic bands for use in surgically tying off small tubular members in animals bodies. More specifically the present invention is particularly directed to elastic bands which are adapted to be used in tying off fallopian tubes, for examples, in human sterilization procedures.

Various procedures have been employed in the past in order to accomplish sterilization by surgically obstructing or tying off fallopian tubes in human females. Such procedures have included for example, cauterization of the fallopian tubes. This procedure however, has the disadvantage of sometimes causing abdominal burns. During the past 50 years the most common technique for tying off fallopian tubes has been the Pomeroy sterilization procedure whereby the fallopian tube is tied with a surgical suture. This procedure has however, had the disadvantage that the thin silk suture actually may cut through the tube. Accordingly an improvement has been to employ cat-gut sutures having a larger diameter than the silk sutures to tie off the fallopian tubes. Although this procedure represents an improvement over the technique of using silk suture it too has not been altogether successful and has resulted in complications due to the tightness required of the suture.

One recent technique which has been developed rather than tie and obstruct the fallopian tubes has been to actually form a loop in the tube and then slip a small elastic band over the loop thereby tying off the fallopian tubes. The bands commonly employed in this procedure and developed specifically for this operation were consisted of a small elastic tube approximately 2 mm thick and having an inside diameter of about 1 mm. Considering that the fallopian tube which is to be tied off has itself a diameter of ⅛ of an inch, it may readily be seen that the use of an elastic band having an internal diameter of only one mm necessarily results in a high degree of constriction. Therefore it is not surprising that patients undergoing sterilization procedures in which the fallopian tubes are tied off by means of these small elastic bands, have experienced a number of post operative complications including abdominal pains which are apparently related to avascular necrosis of the contained segment of the tube within the band. In some instances patients have experienced detatchment and enclosure of the proximal and distal ends of the fallopian tubes at the site of the applied band. Unfortunately, the need to assure that the band remains in place and accomplishes a complete closure of the fallopian tubes without the risk of slipping off, has heretofore necessitated the use of these tight fitting bands having very small internal diameters in the order of 1 mm.

Accordingly, an object of the present invention is to provide an improved elastic band having the configuration and dimensions which permit it to be used to tie off small tubular members having a diameter of about ⅛ inch such as human fallopian tubes without encountering the problems which have been associated with prior art techniques which have used elastic bands having dimensions heretofore described.

Another object of the present invention is to provide an elastic band for use in tying off the fallopian tubes which avoids the problems of the prior art while at the same time remaining firmly in place without a significant hazard of slipping off or otherwise becoming detatched.

According to the present invention an elastic band is provided (for a specific use in tying human fallopian tubes) which varies in thickness from between about 2 to 3.5 mm and has an outside diameter of about 3 to 4 mm and an inside diameter of between 1.4 and 2.2 mm, preferably 1.6 to 2.0 mm. In a preferred embodiment of the present invention, the inside diameter of the tube at either end is slightly smaller than the diameter of the tube at its middle portion over the greater part of its length thereby creating a slight ridge or constricted portion around the inside circumference of the tube at either end. Specifically, while the inside diameter of the tube at its middle portion may range from 1.8 to 2.2 mm the internal diameter at either end of the tube is from 1.4 to 1.8 mm and about 0.2 to 0.6 mm smaller than the middle portion. This slightly more constricted portion of the inside of the tube at both ends may result from the tube gradually tapering from its middle portion to either end portion to a more slightly constricted configuration or may result from a simple ridge being provided at either end of the tube.

This slightly more constricted portion of the inside of the tube at either end is of particular importance with regard to the present invention in view of the significantly larger diameter of the tube as compared with similar tubes used in the prior art. Therefore, while the use of the larger band of the present invention avoids many of the complications which have arisen in the prior art, the problem which has existed in the past of larger diameter tubes or more loosely tied sutures becoming dislocated, is avoided by means of the slightly raised portion or ridge at either end of the tubular band which affectively prevents the band from slipping off of the fallopian tubes. Still another feature of the present invention is that the thickness of the band is preferably at least 50% greater than the inside diameter. This feature of the present invention together with the provision of ridges along the ends of the tube also contributes to the tube remaining in the proper position and helps assure a proper and sufficient enclosure of the fallopian tube.

The present invention will however, be more completely understood by having reference to the drawings.

Figure 1:
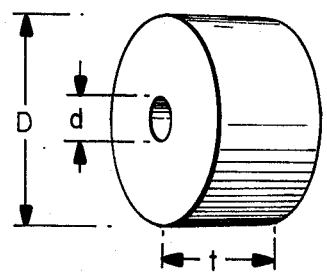
FIG. 1 is a perspective view of elastic bands used to tie off fallopian tubes according to the prior art.

Elastic bands of prior art shown in FIG. 1 which have heretofor been used to tie off human fallopian tubes, typically have a thickness, t, of about 2 mm and an inside diameter, d, of 1 mm. The outside diameter, D, is about 3 mm. and the walls of the hollow, inside portion of the band are straight.

Figure 2:
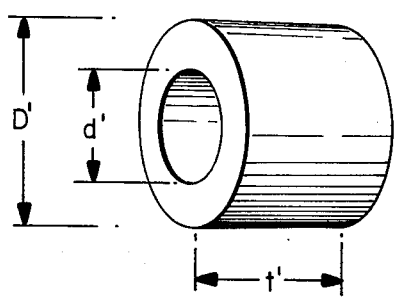
FIG. 2 is a perspective view of the elastic band of the present invention.

One embodiment of the present invention shown in FIG. 2 is an elastic band specifically adapted for tying off human fallopian tubes. In the band shown in FIG. 2, the thickness, t', of the band is 3 mm and the outside diameter, D', is 4 mm. The inner diameter, d', of the band is 2 mm. Thus the band of this invention has a considerably larger inside diameter and greater thickness than prior art bands heretofore employed to tie off human fallopian tubes. With the bands larger inside diameter problems caused by excessive constriction of the fallopian tubes are reduced; however the greater thickness of the band permits its effective retention on the tube.

Figure 3:
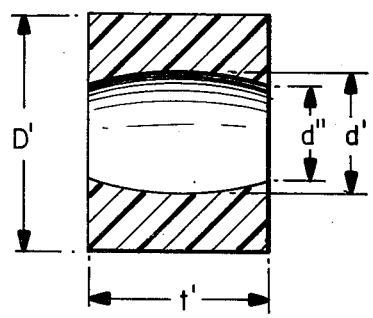
FIG. 3 is a cross-section view of one embodiment of the present invention.
Figure 4:
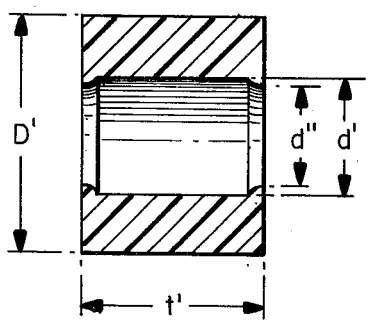
FIG. 4 is a cross-section view of another embodiment of the invention.

FIGS. 3 and 4 illustrate alternative preferred embodiments of the present invention whereby the hollow, inside portion of the band does not have the straight, axially parallel walls of the prior art, but rather, has a slightly larger diameter, d', in the middle portion of the band and a smaller, more constricted diameter, d", at each end. Alternatively, as hown in FIG. 4, the inside walls of the band can be parallel and define a constant diameter, d', for most of the thickness, t', of the band with constrictions provided only at the ends of the band to define the diameter d".

The preferred embodiments of the invention shown in FIGS. 3 and 4 have the advantage that the slightly narrower diameter at either end of the band further reduces any tendencies to slip or come off the fallopian tube once it is in place. Further, this slightly more constricted portion of the band does not cause the band to bind excessively tightly in the manner of prior art devices, but serves only to assist in keeping the improved band of this invention in place.

Application of the elastic bands of the present invention is accomplished using standard techniques and instruments currently in practice in the art.

The bands can be constructed of any of the various elastic materials heretofore employed in similar bands such as silicone rubber material known as Silastic.

Other modifications of the present invention will be apparent to those skilled in the art and are considered to lie within the scope of the invention as defined herein.

I claim:

1. An elastic band adapted for tying off human fallopian tubes, said band consisting of a small, hollow tube whose inside diameter at its midsection is 1.8 to 2.2 mm and whose length is at least about 50% greater than the minimum inside diameter of said tube, the inside diameter of the tube being 0.2 to 0.6 mm. smaller at both ends that at the midsection of the tube.

2. The elastic band of claim 1 which has a outside diameter of 3 to 4 mm.

3. The elastic band of claim 1 wherein the inside diameter of the tube at both ends is 1.4 to 1.8 mm.

4. The elastic band of claim 3 wherein the length of the tube is 2.1 to 3.5 mm.

5. An elastic band for tying off internal tubular members of the human body, said band consisting of a small hollow tube having an outside diameter of 3 to 4 mm., an inside diameter at the midsection of the tube of 1.8 to 2.2 mm. and an inside diameter at both ends thereof which is 0.2 to 0.6 mm. smaller than said midsection inside diameter, and a length which is at least about 50% greater than the minimum inside diameter of said tube.

6. The elastic band of claim 5 which is 2.1 to 3.5 mm. long.

* * * * *